United States Patent
McEwen et al.

(10) Patent No.: US 9,011,483 B2
(45) Date of Patent: Apr. 21, 2015

(54) EXTENDIBLE TOURNIQUET CUFF WITH STABILIZER FOR IMPROVED UTILITY AND SAFETY

(75) Inventors: James A. McEwen, Vancouver (CA); Michael Jameson, North Vancouver (CA); Kenneth L. Glinz, Richmond (CA)

(73) Assignee: Western Clinical Engineering, Ltd., Vancouver (CA)

( * ) Notice: Subject to any disclaimer, the term of this patent is extended or adjusted under 35 U.S.C. 154(b) by 100 days.

(21) Appl. No.: 13/503,966

(22) PCT Filed: Nov. 4, 2010

(86) PCT No.: PCT/CA2010/001767
§ 371 (c)(1),
(2), (4) Date: Apr. 25, 2012

(87) PCT Pub. No.: WO2011/054096
PCT Pub. Date: May 12, 2011

(65) Prior Publication Data
US 2012/0215253 A1   Aug. 23, 2012

Related U.S. Application Data

(60) Provisional application No. 61/258,730, filed on Nov. 6, 2009.

(51) Int. Cl.
*A61B 17/135* (2006.01)
(52) U.S. Cl.
CPC ........... *A61B 17/135* (2013.01); *A61B 17/1355* (2013.01)
(58) Field of Classification Search
CPC .... A61B 17/35; A61B 5/022; A61B 5/02208; A61B 17/132; A61B 17/1322; A61B 17/1325; A61B 17/1327; A61B 5/02233; A61H 9/0078; A61G 7/05769; A61G 7/05776; B65G 17/086
USPC ........... 606/201–203, 204; 24/33 A; 128/875, 128/876, 870, 100.1, 99.1, 102.1; 604/98.01, 118, 379, 509, 101.02, 604/101.05, 148–152; 602/13; 601/134–135
See application file for complete search history.

(56) References Cited

U.S. PATENT DOCUMENTS 4,106,499 A * 8/1978 Ueda .............................. 600/499
4,469,099 A   9/1984 McEwen
5,396,894 A * 3/1995 Eide et al. ..................... 600/499

(Continued)

*Primary Examiner* — Katrina Stransky
*Assistant Examiner* — Sidharth Kapoor
(74) *Attorney, Agent, or Firm* — Hancock Hughey LLP

(57) ABSTRACT

A surgical tourniquet cuff that includes a stabilizer component that facilitates application of an overlapping cuff around the limb of a patient. The stabilizer is fixed to the cuff, and requires no tying or similar user manipulation to secure the overlapping cuff in alignment with the underlying cuff. The stabilizer improves the stability of the inflated cuff to prevent sideways shifting motion of overlapping cuff portions as the cuff is applied to the limb. The stabilizer also provides a handle mechanism to enable the user to snugly apply the overlapping cuff around the patient's limb while the overlapping portions remain properly aligned along their long axes. The stabilizer is designed to also facilitate attaching together two tourniquet cuffs end-to-end, with respective bladders overlapping and in proper alignment so that those attached cuffs can be used as a single, extended surgical cuff applied around a patient's limb.

17 Claims, 6 Drawing Sheets

(56) References Cited

U.S. PATENT DOCUMENTS

| | | | |
|---|---|---|---|
| 5,413,582 A * | 5/1995 | Eaton | 606/202 |
| 5,649,954 A * | 7/1997 | McEwen | 606/202 |
| 5,733,304 A * | 3/1998 | Spence | 606/203 |
| 6,352,074 B1 * | 3/2002 | Okada | 128/98.1 |
| 6,746,470 B2 | 6/2004 | McEwen | |
| 6,942,630 B2 * | 9/2005 | Behan | 602/19 |
| 7,517,341 B2 * | 4/2009 | Barrientos | 604/353 |
| 7,871,387 B2 * | 1/2011 | Tordella et al. | 601/151 |
| 7,955,352 B2 * | 6/2011 | McEwen et al. | 606/202 |
| 2004/0260187 A1 * | 12/2004 | Sano et al. | 600/499 |
| 2006/0287672 A1 | 12/2006 | McEwen | |
| 2007/0135836 A1 * | 6/2007 | McEwen et al. | 606/203 |
| 2007/0219580 A1 * | 9/2007 | McEwen et al. | 606/202 |
| 2008/0251087 A1 * | 10/2008 | Richardson | 128/876 |

\* cited by examiner

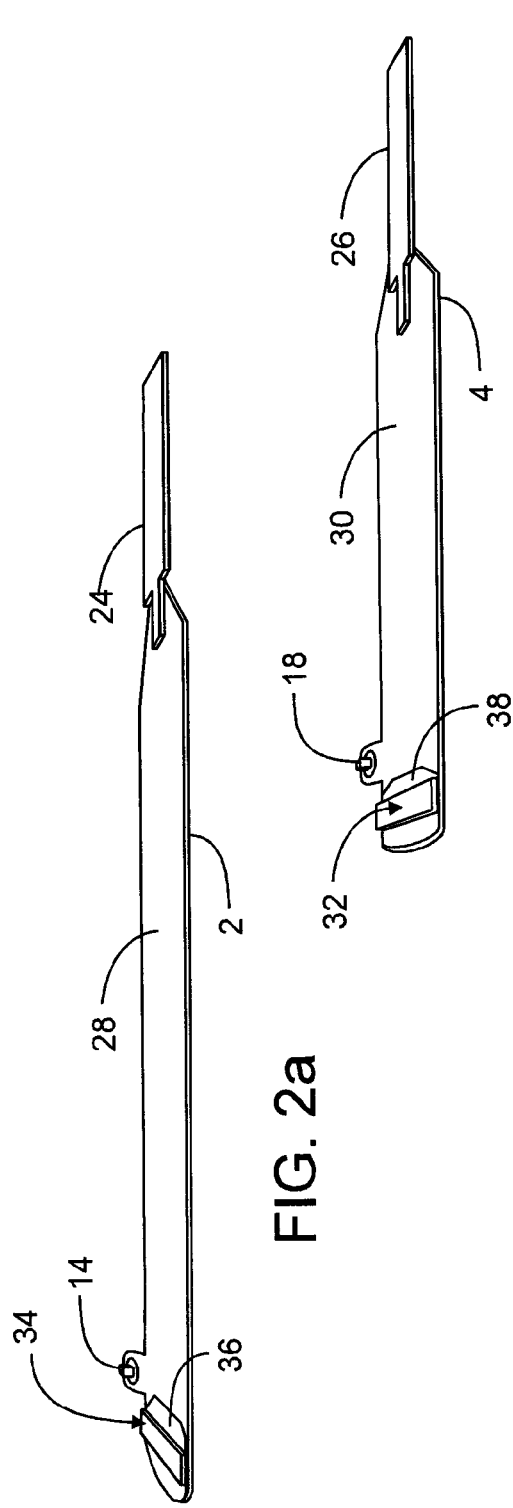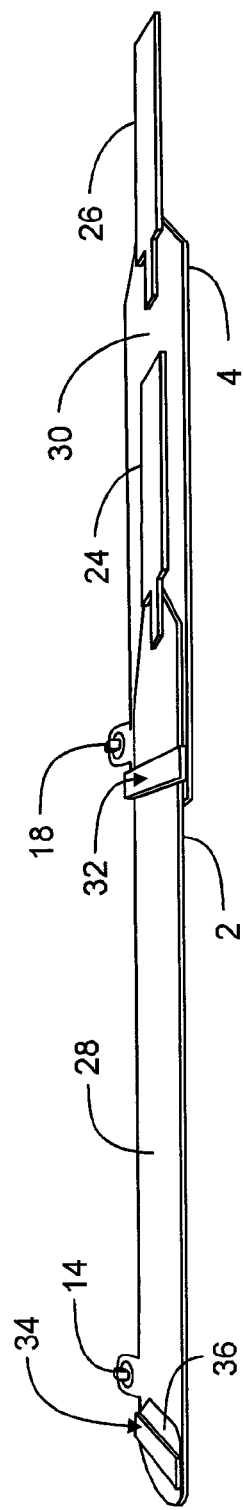

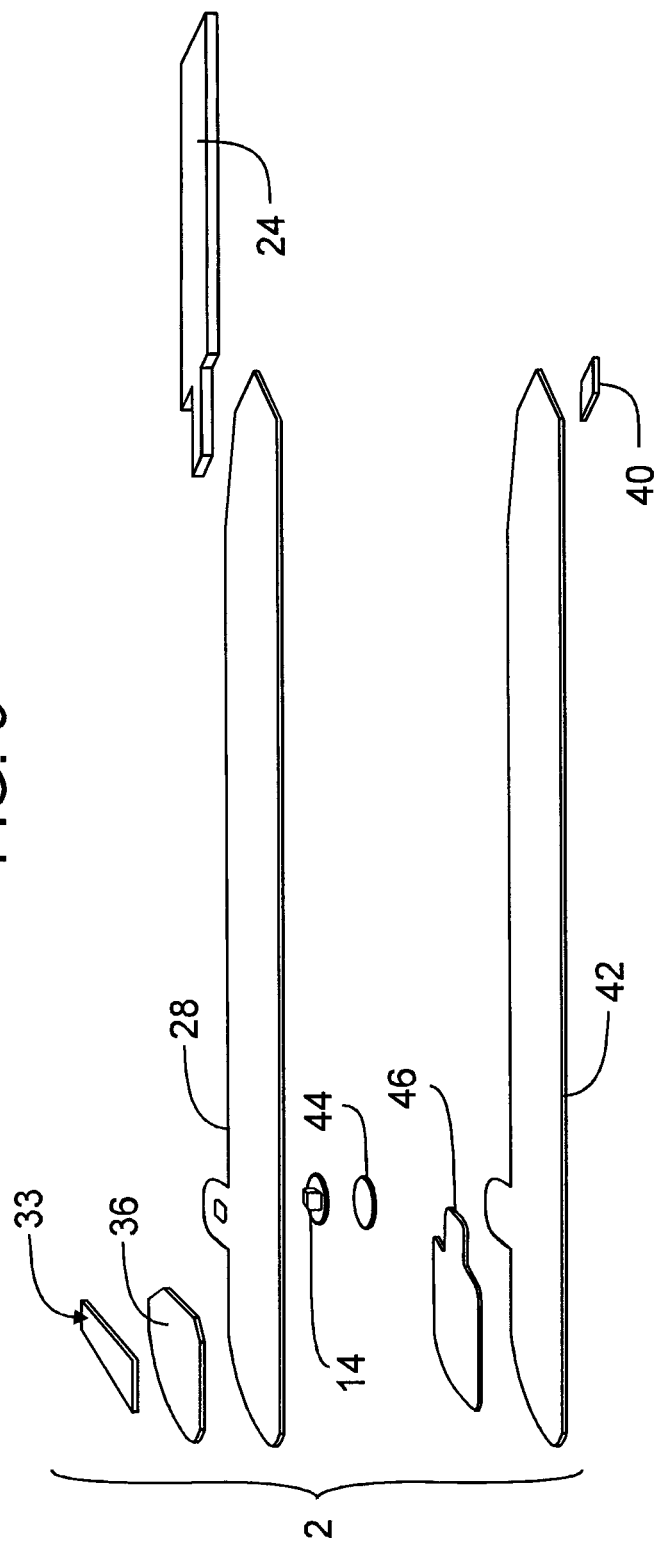

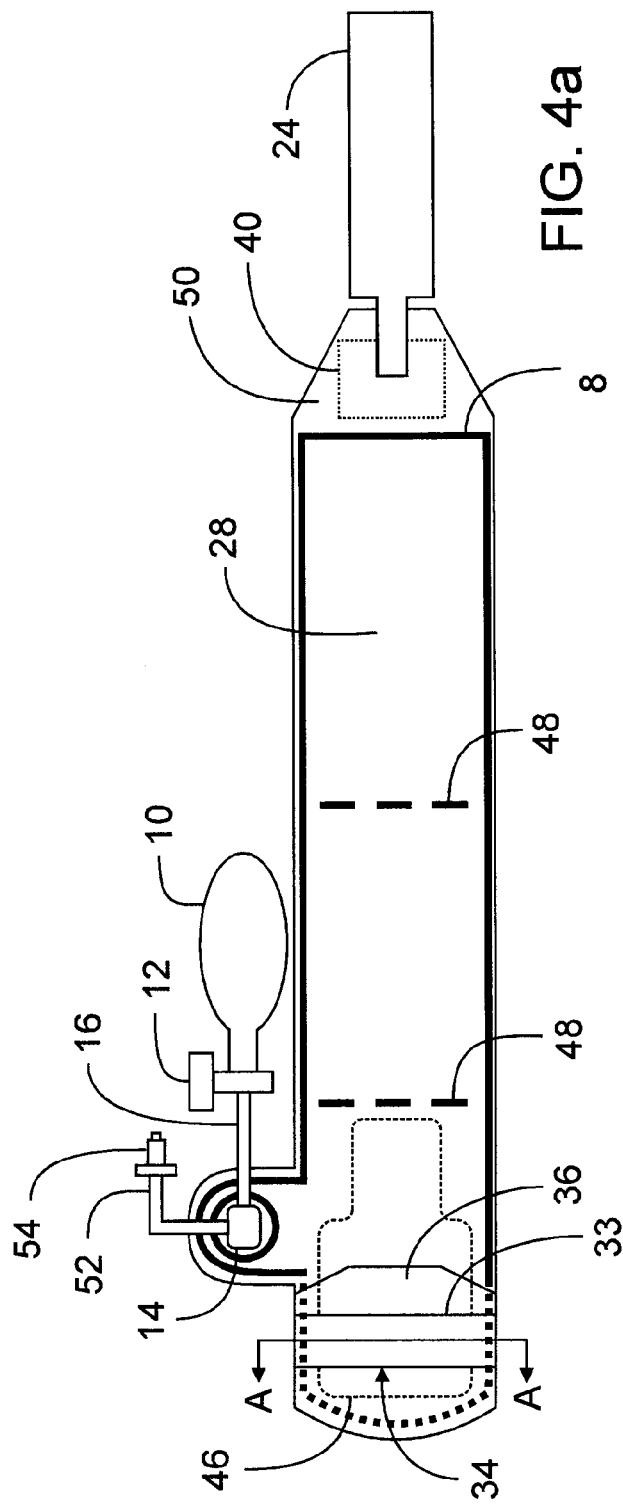

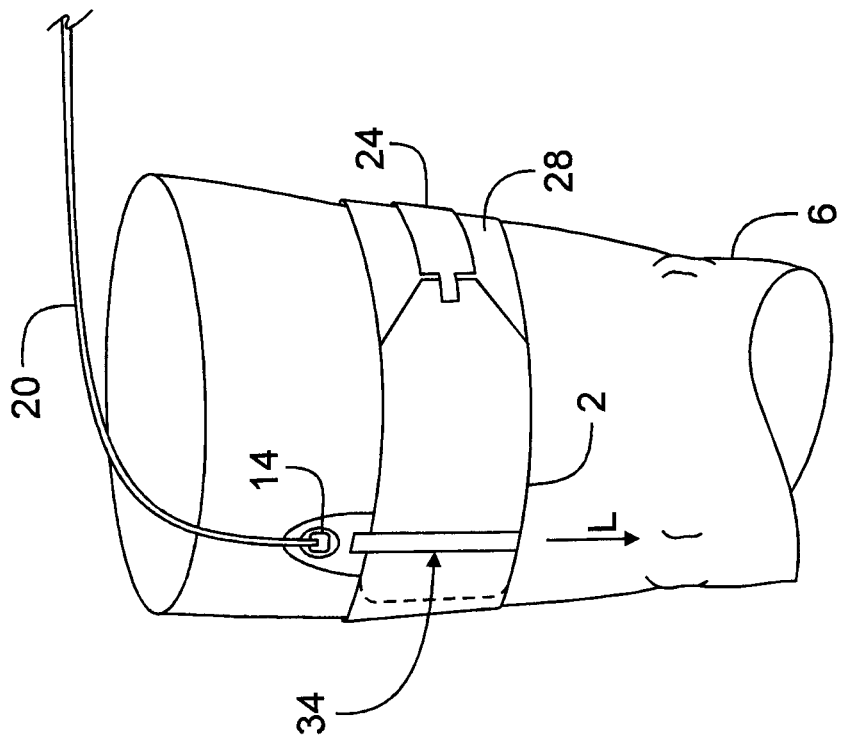
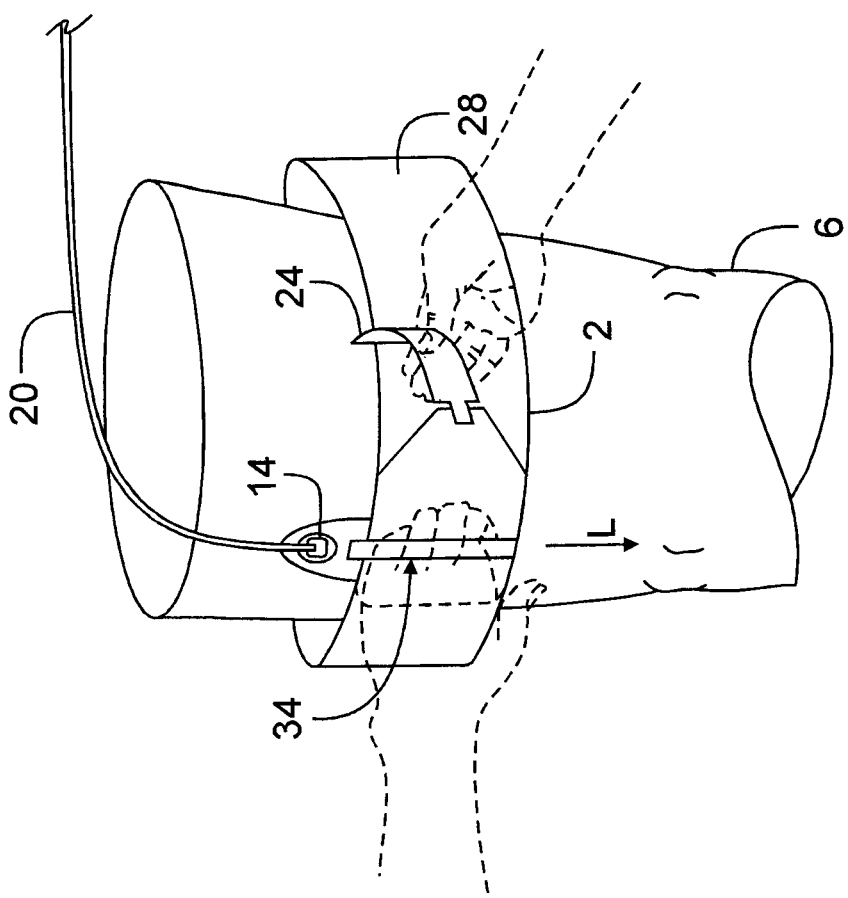

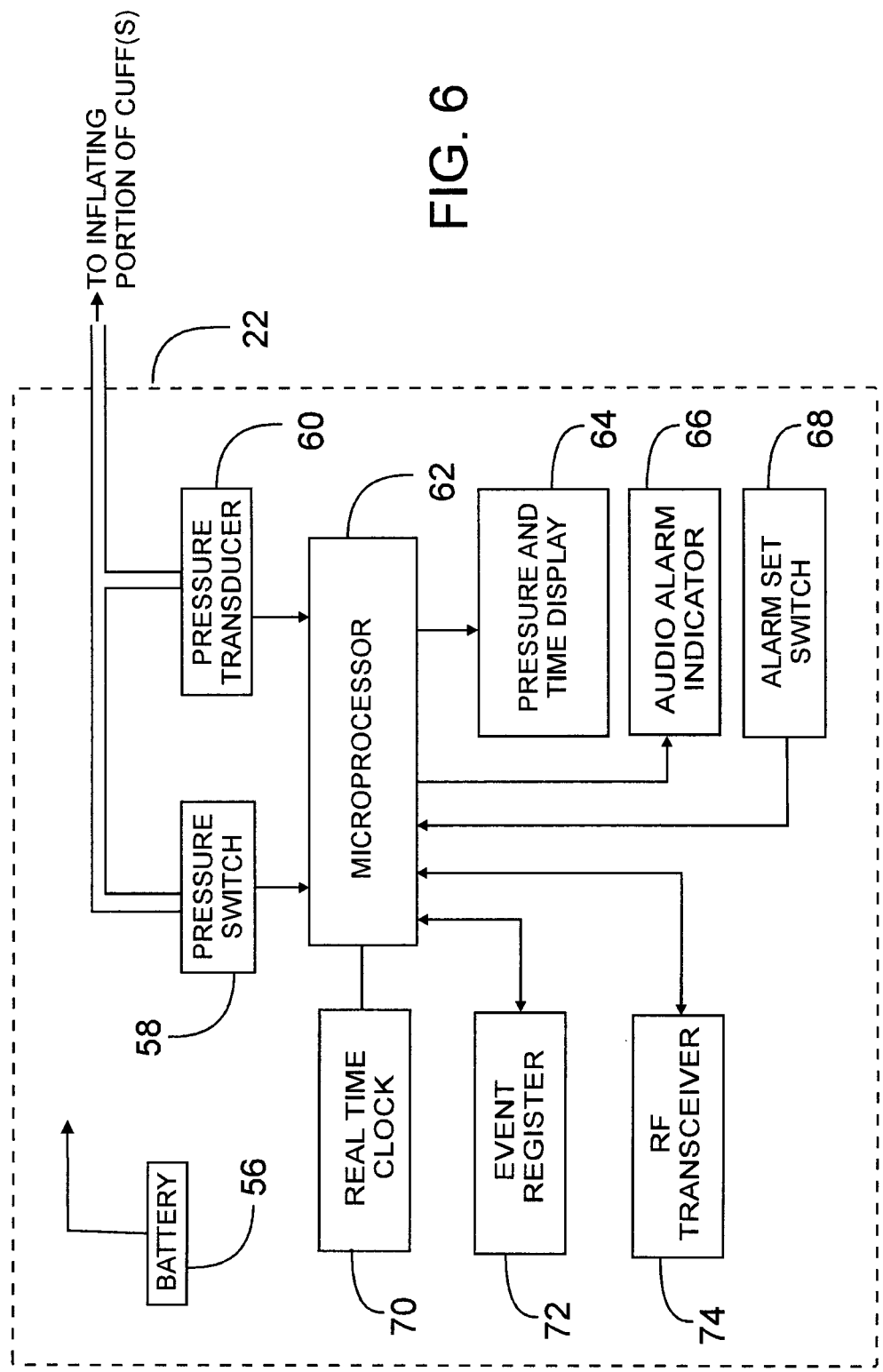

EXTENDIBLE TOURNIQUET CUFF WITH STABILIZER FOR IMPROVED UTILITY AND SAFETY

FIELD OF THE INVENTION

This invention relates to surgical tourniquet cuffs.

BACKGROUND AND SUMMARY OF THE INVENTION

Surgical tourniquet cuffs are applied around the limb of a patient for preventing the flow of arterial blood past the tourniquet to a part of the limb that is positioned in a bloodless surgical field.

Generally, prior art tourniquet cuffs include an inflatable portion, often referred to as a bladder. When such a cuff is applied to encircle a patient's limb, the bladder is inflated to expand by an amount sufficient to apply pressure that prevents arterial blood flow through the limb during the surgery. Specifically, the inflatable cuff is secured to the limb such that pressure on the limb that is generated in the inflated, expanded cuff is transferred to the limb tissue in an amount that is high enough to prevent or occlude arterial blood flow during the surgical procedure.

For safe and uniform application of the pressure for occluding blood flow, it is important that the inflatable bladder of the cuff overlaps itself when applied to encircle the limb. Upon inflation, however, there is a tendency for the overlapping, inflated portions of the cuff to move out of longitudinal alignment. Put another way, the overlapping portion of the cuff may shift laterally or sideways, away from the overlapped portion, which motion can unexpectedly alter the amount or uniformity of the pressure applied to the limb. Such shifting is most likely to occur when the cuff is applied around limbs that taper or are otherwise non-cylindrical in the region where the cuff is applied, as is the limb shown at 6 in FIG. 1.

Some prior art tourniquets include a pair of tie ribbons that hang from the overlapped portion of the tourniquet cuff so that the user (the person applying the cuff) can tie the ribbons together in a knot or bow after the overlapping portion of the cuff is in place. Although such tie ribbons have long been in use, they do not assist the user in properly aligning the overlapping cuff portions prior to tying together the ribbons. Moreover, since the ribbons are typically fabric or other material that can be tied together manually, a user may fail to tie the ribbons tightly enough around the two overlapping cuff portions to prevent the sideways shifting problem noted above. Accordingly, the safety of the cuff in this regard is dependent upon the diligence of the user when securing the tie ribbons.

The present invention is directed to a surgical tourniquet cuff that includes a stabilizer component that facilitates rapid and consistent application of an overlapping cuff around the limb of a patient. The stabilizer is fixed to the cuff, and requires no tying or similar manipulation to secure the overlapping cuff in alignment with the underlying cuff. The stabilizer thus improves the stability of the inflated cuff to prevent the above-mentioned sideways motion when the cuff is inflated and expanded after application to the limb.

The stabilizer offers additional advantages, such as providing a handle mechanism to enable the user to snugly apply the overlapping cuff around the patient's limb while the overlapping portions remain properly aligned along their long axes.

The stabilizer is designed to also facilitate attaching together two tourniquet cuffs end-to-end, with respective bladders overlapping and in proper alignment so that those attached cuffs can be used as a single, extended surgical cuff applied around a patient's limb. This is useful in instances where the patient's limb is so large that a single cuff does not have sufficient length to encircle the limb.

The stabilizer as well as a port that is used for inflating the cuff bladder are located in close proximity at one end of the cuff in a manner that permits the user to positively locate the cuff port (hence the overlapping cuff portions) at a selected anatomical location on the patient's limb, irrespective of variations in the limb circumference from one patient to the next. Such positive location eliminates the need to rotate an attached cuff around a patient's limb to locate the port in a desired location to, for example, best expose the port for connection to an inflation source. Moreover, the port is located so that it does not interfere with overlapping one portion of the cuff upon another portion.

BRIEF DESCRIPTION OF THE DRAWINGS

FIG. 2a is an overall view of the preferred embodiment showing tourniquets of different size.

FIG. 2b is an overall view of the preferred embodiment showing tourniquets of different size releasably connected together.

FIG. 3 is an exploded view of a two-layer tourniquet with partial length internal stiffener.

FIG. 4a is a top view of a two-layer tourniquet with partial length internal stiffener.

FIG. 4b is a view of cross section A of the tourniquet shown in FIG. 4a.

FIG. 5a is a view of a tourniquet being applied to a limb.

FIG. 5b is a view of a tourniquet secured around a limb.

FIG. 6 is a block diagram of the pressure and time indicator module.

DETAILED DESCRIPTION OF THE PREFERRED EMBODIMENT

Figure 1:
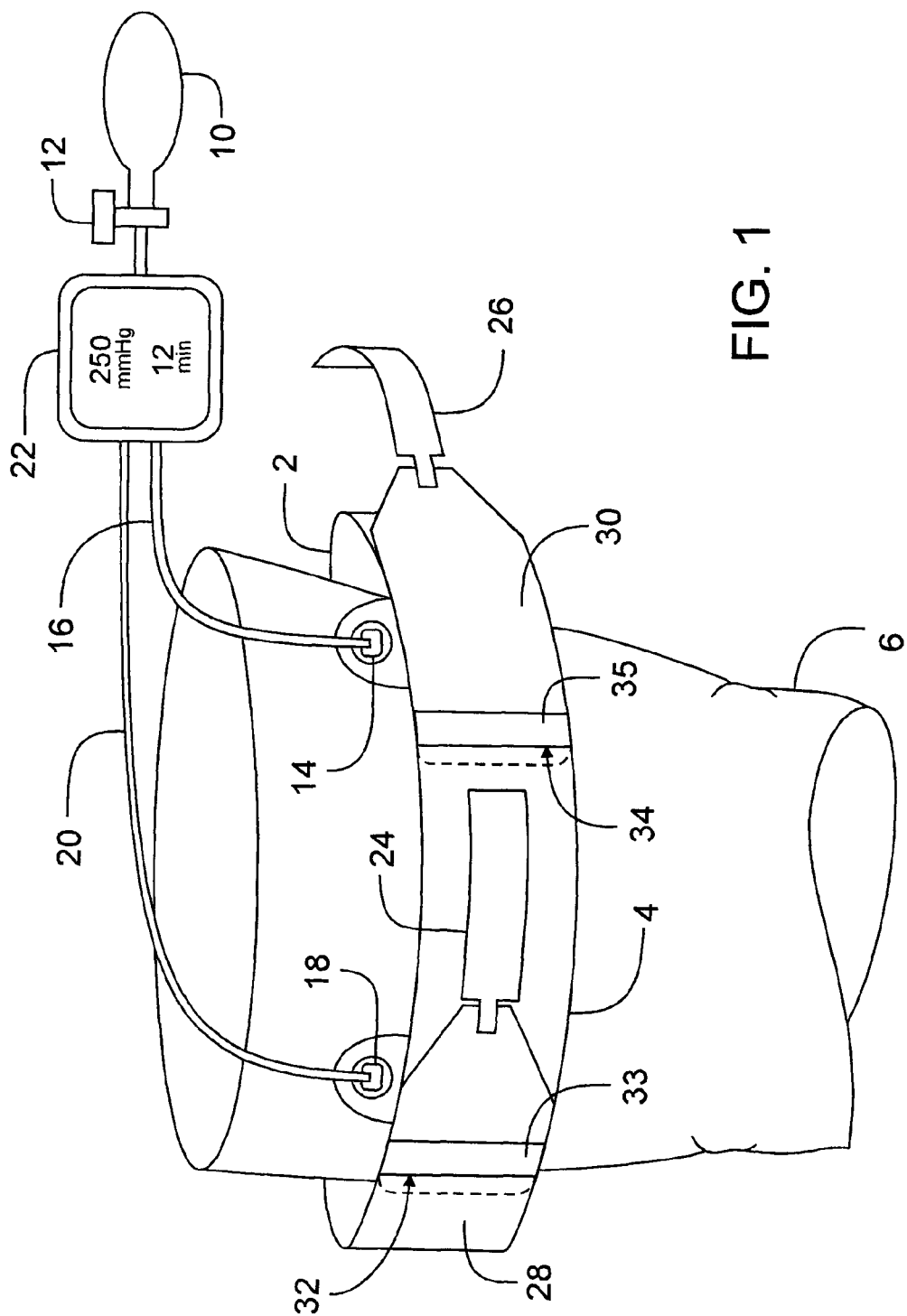
FIG. 1 is a view of the preferred embodiment applied to a large tapered limb.

A specific embodiment illustrated is not intended to be exhaustive or to limit the invention to the precise form disclosed. It is chosen and described in order to explain the principles of the invention and its application and practical use, and thereby enable others skilled in the art to utilize the invention.

Throughout this document the terms 'bond' and 'bonded' will generally refer to processes such as radio frequency (RF) welding, ultrasonic sewing and welding, other forms of plastic welding, adhesive bonding, or solvent bonding selected to be suitable for the materials and coatings chosen for the various components of the cuff. Width and thickness of the bonds are selected to produce a joint of sufficient strength to withstand the stresses produced by typical cuff inflation pressures up to 1000 mmHg at various limb circumferences, and in selected areas, to form a gas impermeable joint between the materials. The terms 'seal' and 'sealed' refer specifically to gas-tight or gas impermeable joints that form inflatable bladders of the preferred embodiment.

FIG. 1 depicts cuff 2 and cuff 4 connected together such that the inflatable bladders of cuff 2 and cuff 4 overlap and completely encircle patient limb 6. Unlike cuffs of the prior art the cuffs of the preferred embodiment, cuffs 2 and 4, are designed such that they may be readily connected together forming an extended cuff when the length of the inflatable bladder of a single cuff is insufficient to completely encircle a limb. When the length of the inflatable bladder of cuff 2 or of cuff 4 is sufficient to completely encircle a limb with a predetermined minimum amount of overlap only a single cuff need be applied to limb 6. When two or more cuffs are connected together in this fashion, they can be handled and applied to the limb as a single cuff.

As shown in FIG. 2a, cuff 2 and cuff 4 are identical in basic construction. To better illustrate the versatility of the preferred embodiment, cuff 2 and cuff 4 are shown and described as having differing overall lengths, cuff 2 has a length greater than that of cuff 4. It will be understood that cuff 2 and cuff 4 may have equal lengths and that cuff 2 may have a length less than that of cuff 4.

Referring again to FIG. 1 the inflatable bladders of cuffs 2 and 4 are simultaneously inflated with pressurized gas until sufficient inward radial compression is applied to limb 6 to prevent arterial blood from flowing distally past cuffs 2 and 4. The inflatable bladder of cuff 2 and 4 is defined by the area within bladder perimeter seal 8 as shown in FIG. 4a, and is substantially the same length and width as the cuff.

The source of pressurized gas for the inflation of cuffs 2 and 4 is manual inflation bulb 10. The user repeatedly squeezes inflation bulb 10 to inflate cuffs 2 and 4. Inflation bulb 10 includes a deflation valve 12 which may be opened to allow the escape of gas thereby depressurizing cuffs 2 and 4. As described further below other sources of pressurized gas may be pneumatically connected to cuffs 2 and 4.

Port 14 and tube 16 form a gas tight pneumatic passageway to the inflatable bladder of cuff 2. Similarly, port 18 and tube 20 form a pneumatic passageway to the inflatable bladder of cuff 4. Tubes 16 and 20 are made from flexible thermoplastic tubing and are permanently bonded to port 14 and 18 respectively.

Tubing 16 and tubing 20 are pneumatically connected to indicator module 22 and inflation bulb 10. Indicator module 22 is similar to that described in U.S. Pat. No. 6,746,470 and herein incorporated by reference, and is further described below. Indicator module 22 monitors the pressure of gas within cuffs 2 and 4 and indicates this pressure and elapsed time that the cuffs have been pressurized to the user. Indicator module 22 also operates to alert the user if predetermined alarm conditions are present. Indicator module 22 may be pneumatically connected to only a single cuff such as cuff 2 when the inflatable bladder of the cuff has sufficient length to completely encircle the limb.

As shown in FIG. 1 cuffs 2 and 4 are secured around limb 6 by securing straps 24 and 26. Securing strap 24 is non-releasably attached to a non-inflating region of cuff 2 near an end edge. Similarly, securing strap 26 is non-releasably attached to a non-inflating region of cuff 4 near an end edge. Securing straps 24 and 26 have fastening portions which releasably engage with the outer surfaces of cuffs 2 and 4 and bending portions which permit the fastening portions to be positioned such that they can completely engage the outer surface within the side edges of the cuff. In the preferred embodiment the outer surface of cuffs 2 and 4 and fastening portions of securing straps 24 and 26 are formed from hook and loop Velcro-type materials. Loop type materials comprise loop layer 28 that forms the outside surface of cuff 2 and loop layer 30 that forms the outer surface of cuff 4. Hook type materials comprise the fastening portions of securing strap 24 of cuff 2 and securing strap 26 of cuff 4. The hook materials used for securing straps 24 and 26 are selected to have significantly greater shear strength when engaged with loop material (45 P.S.I shear) than the materials typically used in prior art cuffs (15 P.S.I shear). The greater shear strength permits the length of securing straps 24 and 26 to be reduced from that what would be otherwise necessary to secure cuff 2 around limb 6 had typical strength materials been selected.

To connect cuffs 2 and 4 together as shown in FIG .1, securing strap 24 of cuff 2 is first slid through a loop or slot of an overlapping-bladder stabilizer 32 of cuff 4 until the inflatable bladder of cuff 2 overlaps the inflatable bladder of cuff 4, securing strap 24 is then engaged with loop layer 30 of cuff 4. Stabilizer 32 of cuff 4 maintains the overlapped portion of cuff 2 in alignment with cuff 4 and prevents it from moving laterally or sideways (where the sideways direction is oriented vertically in, for example, FIGS. 1 and 5b) with respect to cuff 4 during application to limb 6 and when cuffs 2 and 4 are inflated. To secure the connected cuffs around limb 6 as shown in FIG. 1, securing strap 26 of cuff 4 is slid through the slot of overlapping-bladder stabilizer 34 of cuff 2 and pulled until the inflatable bladder of cuff 4 overlaps the inflatable bladder of cuff 2; stabilizer 34 is used as a handle by the user, as shown in FIG. 5a, to apply tension to the cuffs for a snug fit to the limb prior to engaging securing strap 26 to loop layer 28 of cuff 2. During application of the connected cuffs to limb 6, stabilizer 34 maintains the cuffs in alignment and prevents cuff 2 from moving laterally with respect to cuff 4 when cuffs 2 and 4 are inflated. When cuff 2 alone is applied correctly to a limb such that the inflating bladder overlaps itself, stabilizer 34 maintains the overlapping portion of the cuff in alignment with the non-overlapped portion during application and when cuff 2 is inflated. Stabilizers 34 and 32 each include an elongated strip 35, 33 (FIG. 1), the opposite edges of each strip being non-releasably attached (as by bonding) to the side edges of cuffs 2 and 4, respectively, near the cuff end edge that is opposite to the end of the cuff that the securing strap is attached to as shown in FIGS. 1, 2, 3, 4a and 4b. Stabilizers 32 and 34 are substantially the same length as the cuff width. As best shown in FIG. 4B, a strip 35 defines in part an enclosed slot 37 adjacent to the layer 28 that forms a top surface of the cuff. The cross-sectional area of the slot generally conforms to that of a substantially deflated cuff.

Stiffeners located in the region where stabilizers 32 and 34 attach to the side edges of cuff 4 and 2 insure that this region remains substantially flat while a securing strap is passed through the slot 37 of the stabilizer and thereby facilitates the rapid application of the cuff to the limb. The stiffener element is described further below.

An engagement shield 36 is interposed between the outer surface of loop layer 28 (top surface of cuff 2) and the inner surface of the stabilizer strip 35. The strip 35 in combination with engagement shield 36 forms the stabilizer slot 37 as shown in FIGS. 1 and 4b within the width of the cuff to align the long axes of the cuffs. The cuff-enclosing slot 37 also stabilizes the overlapping portions of the cuff so that those portions will not shift or slide laterally (sideways) relative to one another. The engagement shield 36 acts to prevent the hook material of securing strap 26 from engaging with the surface of loop layer 28 of cuff 2 as securing strap 26 is slid through slot 37. Engagement shield 36 is manufactured from an adhesive backed polypropylene label material or similar material that is incompatible with the hook material of securing strap 26. The width of engagement shield 36 is substantially the same as the width of cuff 2, the length of engagement shield 36 is selected to define a predetermined minimum overlap between the inflatable bladders of cuffs 2 and 4 when cuffs 2 and 4 are connected together.

Stabilizer 34 and engagement shield 36 may be printed with graphic marks, text and symbols to provide instruction on the proper application of the cuff to a user. To simplify manufacturing and reduce costs, engagement shield 36 and stabilizer 34 may be combined in a single structure that is attached near the end edge of cuff 2. The single structure may also be integrated with the material that forms a port. Engagement shield 38 of cuff 4 is identical to engagement shield 36.

The inflatable bladders of cuff 2 and cuff 4 are extended beyond a side edge of the cuffs at a location near the bladder stabilizer to form an attachment region for port 14 on cuff 2 and port 18 on cuff 4. (It is noteworthy here that in this description the notion of cuff "width" is not intended to include the extension provided by the attachment region just mentioned.) The distance between the location of port 14 along the side edge of cuff 2 with respect to the non inflating region of the end edge where securing strap 24 is attached defines the maximum amount of overlap between cuff 2 and cuff 4 when connected together and the maximum amount of overlap upon itself when cuff 2 is used alone.

FIGS. 5a shows cuff 2 being applied to limb 6 and FIG. 5b shows cuff 2 secured around limb 6. In FIGS. 5a and 5b the location of a predetermined anatomical landmark on limb 6 is indicated by arrow L. The close proximity of port 14 to stabilizer 34 and the end edge of cuff 2 permits a user to position the port location relative to a predetermined anatomical landmark on limb 6 and maintain during cuff application both the location of the port and the location where the inflatable bladder begins to overlap upon itself in position relative to the predetermined anatomical landmark on limb 6 regardless of the circumference of limb 6, as shown in FIGS. 5a and 5b. Unlike prior art cuffs that typically have ports located between the side edges of the cuff and near the securing strap attachment, the location of the port on the limb relative to the location where the bladder overlaps upon itself varies as a function of limb circumference and the user can not maintain both in position relative to a predetermined anatomical landmark on limb 6 during cuff application. To better illustrate the advantage of locating stabilizer 34 near port 14 of cuff 2, stabilizer 34 is shown in FIGS. 5a and 5b in an alternate position directly opposite port 14. In this alternate position one edge of elongated strip 33 is attached near a side edge of cuff 2 and the opposite edge is attached slightly within the above-mentioned region for attachment of port 14. In this arrangement the long axis of the strip 33 (hence, the underlying slot 37) and the port 14 are laterally aligned (that is, aligned in a direction perpendicular to the long axis of the cuff), and the slot width better conforms to the width of the cuff. Accordingly, the overlapping cuff can be pulled through the slot while completely flat and without the strip interfering with the cuff edges as the cuff is pulled through the slot. The slot width conformance with the cuff width will, as in the other arrangement, prevent any sideways shifting of the overlapping cuff portions.

Limb 6 shown in FIG. 1 is typical of the thigh portion of a larger lower limb that has a substantially tapered shape. Cuffs 2 and 4 are rectangular in shape. When cuffs 2 and 4 are snugly applied to limb 6 the overlapped sections may not be directly in line with each other thereby preventing the securing straps from completely engaging the loop layers on cuff 2 and cuff 4. To allow complete engagement of the securing straps with the loop layers of cuff 2 and 4 securing straps 24 and 26 include a bending portion that permit securing straps 24 and 26 to twist thereby allowing them to completely engage with the loop surfaces of cuff 2 and 4 while maintain their substantially flat shape.

Securing straps 24 and 26 are formed from substantially flat flexible inextensible materials, such as the nylon hook material that is commonly used in hook and loop Velcro-type fastening applications. As described above, securing straps 24 and 26 have a fastening portion and a bending portion. The bending portion of securing strap 24 and 26 has a width less than the width of the fastening portion; the reduced width of the bending portion allows the bending portion to twist out of its substantially flat shape to facilitate positioning of the fastening portion. It will be appreciated that the fastening portion and bending portion of securing straps 24 and 26 may be comprised of different materials that are permanently joined together to form the securing strap, for example the bending portion may be comprised of a material that is substantially more flexible than the material comprising the fastening portion. For further example, securing straps 24 and 26 could be comprised of a bending portion formed from a segment of grosgrain ribbon which is permanently bonded to a fastening portion formed from a segment of nylon hook material.

FIG. 3 is an exploded view of the individual components of cuff 2 that are bonded together to form cuff 2. For clarity, tube 16, indicator module 22 and inflation bulb 10 are not shown in FIG. 3. To reduce the cost of manufacturing cuff 2 it is desirable to manufacture cuff 2 in a single dielectric RF welding operation. This requires selected layers of cuff 2 comprising thermoplastic polymers to be welded together and selected components of cuff 2 be prevented from welding at selected surfaces as described below.

Loop layer 28 forms the top surface of cuff 2 and is a flexible knit loop nylon material (for example, 200 Series Loop Material, Aplix Inc., Charlotte, N.C. 28241) adapted for secure engagement with securing strap 24 and secondary fastener 40. It will be appreciated that loop layer 28 may be made from other types of flexible sheet materials to which Velcro-type materials have been permanently attached and that the sheet material may not be completely covered by the Velcro-type material. For instance, a portion of the loop layer underlying the stabilizer strip may be free of any loop material, which may eliminate the need for the engagement shield discussed above.

The inner surface of loop layer 28 which has not been adapted for hook engagement is coated with a thermoplastic polyurethane polymer. The thermoplastic polymer coating prevents the passage of gas through loop layer 28 and allows loop layer 28 to be welded to bottom layer 42 in selected areas to form the inflatable bladder of cuff 2. Bottom layer 42 is made of a flexible woven nylon cloth coated on one surface with a thermoplastic polymer (for example, 70 Denier nylon cloth coated with thermoplastic polyurethane 0.004" thick).

In the preferred embodiment, the thermoplastic coating on loop layer 28 and thermoplastic coating on bottom layer 42 is polyurethane. It will be appreciated by those skilled in the art that other thermoplastic polymers may be selected as coatings on loop layer 28 and bottom layer 42 provided they can be joined with sufficient strength to maintain the integrity of cuff 2 when inflated.

Port 14 is made of a thermoplastic polymer and has a flange that is compatible with and can be sealed to the thermoplastic coating of loop layer 28 to form a gas-tight seal. Port mask 44 is interposed between port 14 and bottom layer 42. In the preferred embodiment, port mask 44 is formed from the same material as bottom layer 42.

To permit the cost effective manufacture of cuff 2 it is desirable to form the seals bonding loop layer 28 to bottom layer 42 and port 14 to the coated surface of loop layer 28 in a single dielectric welding operation. To prevent port 14 from bonding to bottom layer 42 during the dielectric welding operation port mask 44 is placed below port 14 such that the polyurethane coated surface of port mask 44 is facing the polyurethane coated surface of bottom layer 42 and the nylon cloth surface of port mask 44 surface is facing port 14. During the welding operation, port mask 44 bonds to bottom layer 42 and port 14 bonds to the polyurethane coated surface of loop layer 28. The material comprising port 14 is not compatible with the nylon fabric surface of port mask 44 thereby preventing port 14 from bonding to the top surface of port mask 44 during the welding operation.

FIG. 3, FIG. 4a and FIG. 4b show stiffener 46 contained within a portion of the inflatable bladder of cuff 2. Stiffener 46 is made from a thermoplastic material such as 0.020" high-density polyethylene. The shape of stiffener 46 in the preferred embodiment has been specifically chosen to help ensure that the region defined by engagement shield 36 of cuff 2 remains substantially flat as the user applies tension to stabilizer 34 while snugly apply cuff 2 to limb 6, and to conform to smaller circumference limbs without pinching the underlying soft tissues of the limb when cuff 2 is snugly applied to the limb.

Stiffener 46 has a first section that is substantially the same width as the inflating bladder of cuff 2 and defined by perimeter seal 8, the length of this section is substantially the same length as engagement shield 36. This first section of stiffener 46 helps maintain the region of engagement shield 36 to remain flat as the user applies cuff 2 to limb 6. The second section of stiffener 46 has substantially less width than the first section. This narrower section allows stiffener 46 to conform to smaller circumference limbs without pinching the underlying soft tissues of the limb when cuff 2 is snugly applied to the limb. The overall length of stiffener 46 is less than half the length of the inflatable bladder of cuff 2.

For tactical situations where cuff 2 may be carried by the user or is part of a compact kit of supplies carried by a medic, it is particularly important that the packed size and overall weight of cuff 2 be minimized. Unlike cuffs of the prior art which contain a stiffener that is substantially equivalent to the length of the inflatable bladder and must be rolled for storage to prevent damage to the stiffener, the length and widths of stiffener 46 of the current invention are predetermined to ensure that a region of cuff 2 as defined by engagement shield 36 remains substantially flat during application and to permit cuff 2 to be folded into a small package without damage to stiffener 46. Alternatively, for non-tactical situations cuff 2 may be constructed from three layers of material with a stiffener that has a length equivalent to the bladder length and is located between a non-inflating upper cuff layer and an inflatable bladder formed between middle and lower cuff layers, as for example, is described by McEwen in U.S. Patent Application No. US 2006/0287672 A1.

FIG. 3 shows secondary fastener 40 which is comprised of hook material. Secondary fastener 40 on cuff 2 is attached to the outer surface of bottom layer 42 and engages with the loop layer of cuffs 2 and 4 when connected together or with loop layer 28 when only cuff 2 is applied to a limb. Secondary fastener 40 assists the user during cuff application and along with stabilizer 34 helps maintain alignment between cuff 2 and cuff 4 when cuff 2 and cuff 4 are joined together. The hook material of secondary fastener 40 has significantly lower shear and peel strengths than that of the hook material of securing straps 24 and 26. The properties of the hook material selected for secondary fastener 40 allow it to be easily engaged and disengaged from loop layer 28 so that the cuff may be easily positioned on the limb prior to being secured. The additional fastening surface area provided by secondary fastener 40 and the properties of the hook material selected for securing straps 24 and 26 allows the length of hook securing straps 24 and 26 to be reduced from what otherwise would be required to maintain cuff 2 and cuff 4 secured around a limb. Shorter securing straps allow cuff 2 to be applied quickly to a limb and allow cuff 2 to be folded into a small package which is desirable in tactical situations. Secondary fastener 40 also improves the stability of cuffs 2 and 4 on the limb by resisting lateral movement between the two overlapped cuff ends.

During manufacturing of cuff 2 as shown in FIG. 3 and FIG. 4a stiffener 46 and port mask 44 is positioned between loop layer 28 and bottom layer 42, port 14 is inserted into an opening in loop layer 28. In a single RF welding process, port 14 is sealed to loop layer 28 and port mask 44 is bonded to bottom layer 42, and loop layer 28 is sealed to bottom layer 42 by bladder perimeter weld 8 and flute welds 48 forming the inflatable bladder of cuff 2, Flute welds 48 constrain the inflatable bladder of cuff 2 when inflated and prevent relative lateral movement between selected areas of loop layer 28 and bottom layer 42 reducing the tendency of cuff 2 to roll along the longitudinal axis of the limb. Perimeter weld 8 and flute weld 48 constrain the position of stiffener 46 within the inflatable bladder of cuff 2.

Non-inflating region 50 shown in FIG. 4a, defines a non-inflating region near an end edge of cuff 2. Secondary fastener 40 is attached to the outer surface of bottom layer 42 by stitching around its perimeter within the non-inflating region. The bending portion of securing strap 24 is attached to the outer surface of loop layer 28 within non-inflating region 50.

Engagement shield 36 and stabilizer 34 are attached to loop layer 28. Tubing 16, indicator module 22, and inflation bulb 10 are attached to port 14 completing construction of cuff 2.

It will be apparent that secondary fastener 40 and securing strap 24 may be attached by other mechanical fastening means or by welding or adhesives. It will also be apparent that the inflatable bladder of cuff 2 could be extended eliminating non-inflating region 50.

In FIG. 4a port 14 is shown with tubing 16 connected to inflation bulb 10 and deflation valve 12 for the manual control of pressure within the inflatable bladder of cuff 2. To enable the pressure within the inflatable bladder of cuff 2 to be regulated automatically, a pneumatic connection to the inflating bladder of cuff 2 is made by tubing 52 and connector 54 (PMCD2202, Colder Products Company, St. Paul Minn.). Connector 54 incorporates a shut off valve that remains closed when connector 54 is not mated with a properly configured mating connector, thereby preventing the escape of gas from cuff 2 when it is not connected. Connector 54 is designed to be compatible with conventional surgical tourniquet systems that automatically regulate pressure and allows cuff 2 to be connected to these systems without any substantial loss of pressure within the inflatable bladder of cuff 2 or removal of cuff 2 from the limb if the patient is transferred to a more sophisticated care setting where a conventional surgical tourniquet system (such as that described by McEwen in U.S. Pat. No. 4,469,099) is available. Prior art tourniquets do not include connectors with integral shut off valves as it would be unsafe to do so as prior art cuffs do not include a permanently attached separate means of manual pressure control such as deflation valve 12 and inflation bulb 10.

A block diagram of indicator module 22 is shown in FIG. 6 and described below. Indicator module 22 indicates cuff pressure (the pressure of gas within the inflatable bladder of cuff 2, and cuff 2 and cuff 4 when two cuffs are used) and elapsed inflation time (the duration of time that the cuff pressure has exceeded a predetermined pressure threshold) to the user of cuff 2. Indicator module 22 also operates to alert the user and provide instructions if predetermined alarm conditions are present. As shown in FIG. 6 indicator module 22 includes the following components: battery 56, pressure switch 58, pressure transducer 60, microprocessor 62, pressure and time display 64, alarm indicator 66, alarm set switch 68, real time clock 70, event register 72 and RF transceiver 74.

To preserve the life of battery 56 and allow cuff 2 to be stored unused for long periods time microprocessor 62 operates in a low power standby mode (sleep mode) and de-energizes the other electronic components of indicator module 22 when indicator module 22 is not in use to monitor pressures within cuff 2. In the preferred embodiment microprocessor 22 and other components are configured to draw a minimum amount of current from battery 56.

Pressure switch 58 is a normally open switch that communicates pneumatically with the inflatable bladder of cuff 2 and closes when the pressure within the inflatable bladder exceeds a predetermined threshold pressure that indicates that cuff 2 is in use and is being inflated. In the preferred embodiment the predetermined threshold pressure that pressure switch 58 closes at is 20 mmHg.

The closing of pressure switch 58 signals microprocessor 62 to wake up from sleep mode and operate normally. Microprocessor 62 energizes pressure transducer 60, display 64 and the other components of indicator module 22. Microprocessor 62 is also signaled to wake up from sleep mode by a user activating alarm set switch 68 and may also be signaled to wake up periodically at predetermined times by real time clock 70. Microprocessor 62 remains active and operating normally until pressure switch 58 has been open (cuff 2 depressurized) for a predetermined deactivation time interval. In the preferred embodiment microprocessor 62 remains active for 60 minutes after cuff 2 has been depressurized.

Pressure transducer 60 communicates pneumatically with the inflatable bladder of cuff 2 and provides an indication of the pressure within cuff 2 to microprocessor 62. Microprocessor 62 is programmed to determine elapsed inflation time by measuring the duration of time that the pressure in cuff 2 has exceeded a predetermined pressure threshold, as indicated by pressure transducer 60.

Display 64 is controlled by microprocessor 62 to indicate cuff pressure, elapsed inflation time, and other parameters and instructions to the user.

Alarm indicator 66 provides an audible and visual indication of alarm conditions to the user. Microprocessor 62 activates alarm indicator 66 when certain predetermined conditions of cuff pressure and elapsed inflation time exist. For example, if the pressure in cuff 2 has been inflated above a predetermined threshold and has remained above this threshold continuously for a predetermined elapsed time interval, alarm indicator 66 is activated to warn the user to deflate cuff 2 for a reperfusion period of 5 to 10 minutes to reduce the extent of avoidable ischaemic damage to the limb. A suitable elapsed time interval is 2 hours, suggested by some in the surgical literature as a generally safe period for continuous occlusion in a limb. Alarm indicator 66 may also be activated by microprocessor 62 if unusually high pressures are detected in cuff 2 (for example pressures greater than 400 mmHg) to warn the user that the pressure may be higher than necessary and that the risk of limb injury has increased.

Microprocessor 62 may also be programmed to monitor rate of pressure change and activate alarm indicator 66 if a predetermined rate of pressure decline is exceeded, which may mean that cuff 2 is failing to maintain pressure due to damage or improper application.

Microprocessor 62 is programmed to monitor the difference between a reference pressure level and the current pressure in cuff 2 and activate alarm indicator 66 if a predetermined pressure difference is exceeded. To set the reference pressure level a user first inflates cuff 2, when the pressure within cuff 2 as indicated by module 22 is at the desired reference pressure level, the user depresses alarm set switch 68 which signals microprocessor 62 to set the reference pressure level to the pressure level sensed by pressure transducer 60 at the time alarm set switch 68 is depressed. For example when cuff 2 is inflated to sufficient pressure to stop bleeding, alarm set switch 68 may be depressed and alarm indicator 66 will be activated if the pressure in cuff 2 falls a predetermined amount below or rises a predetermined amount above the reference pressure, alerting the user to check for bleeding and adjust the inflation pressure if required.

Indicator module 22 includes real time clock 70 and event register 72. Real time clock 70 maintains the current date and time. Microprocessor 62 operates event register 72 to maintain a detailed record of pressures, inflation times and alarm conditions. In the preferred embodiment events are defined to be: actions by a user to inflate or deflate cuff 2, adjust the reference pressure level, and alarm events resulting from microprocessor 62 activating alarm indicator 66. Microprocessor 62 records an event by communicating to event register 72 the time of the event from real time clock 70, a value indicating which of a predetermined set of events occurred, and the value at the time of the event of the pressure sensed by pressure transducer 60, the reference pressure level and the elapsed inflation time.

Indicator module 22 includes RF transceiver 74 to allow wireless communication with external information networks or other external monitoring equipment. Microprocessor 62 may via RF transceiver 74 establish a communication link with an external device and transmit the pressure level within cuff 2 as indicated by pressure transducer 60 and the elapsed inflation time to an external device. Microprocessor 62 may also transmit the events and associated data stored within event register 72, this allows users to obtain a complete history of the pressures applied by cuff 2 to limb 6.

We claim:

1. An elongated, inflatable tourniquet cuff for encircling a limb of a patient, the cuff having a length and a width and a top surface, the cuff comprising:
    a first port for inflating the inflatable tourniquet cuff;
    a first end having a fastener extending therefrom;
    a second end opposite the first end and including a first slot through which fits the fastener and first end of the inflatable tourniquet cuff so that a first inflatable portion of the cuff is extendable through the first slot to overlap a second inflatable portion of the cuff resulting in an overlapped surface between the first inflatable portion and second inflatable portion, such that the inflatable tourniquet cuff, including the overlapping first and second inflatable portions, encircles a limb with the fastener located between the first and second ends to engage the top surface of the cuff; the cuff further comprising:
    an elongated inflatable first cuff member including:
    an inflatable first end having a second fastener extending therefrom;
    a second end opposite the first end and including the first slot; the first port connected to the inflatable first cuff member;
    an elongated inflatable second cuff member including:
    an inflatable first end from which extends the fastener;
    a second end opposite the first end and including a second port connected to the second cuff member for inflating the second cuff member;
    wherein the overlapped surface long axes of the first inflatable cuff member and second inflatable cuff members are aligned,
    the second end of the second cuff member also including a second slot through which extends the inflatable first end and second fastener of the first cuff member; wherein the second fastener extending from the first cuff member engages the second cuff member, thereby connecting together the first and second cuff members to comprise the inflated tourniquet cuff.

2. The cuff of claim 1 wherein the first slot is sized to enclose the first cuff portion to prevent the first and second overlapping, inflatable cuff portions from moving sideways relative to one another.

3. The cuff of claim 1 wherein the first slot is sized and arranged to align the long axes of the first and second overlapping, inflatable cuff portions.

4. The cuff of claim 1 further comprising an elongated strip attached at opposing edges thereof across the width of the cuff top surface to define the first slot.

5. The cuff of claim 1 further comprising an engagement shield to prevent the fastener from engaging the top surface of the cuff when the fastener is slid through the first slot.

6. The cuff of claim 5 wherein the engagement shield is integrally formed with an elongated strip that is attached at opposing edges thereof across the width of the cuff top surface to define the first slot.

7. The cuff of claim 1 further comprising a stabilizer member attached to the second end of the cuff within the width of the cuff and defining the first slot.

8. The cuff of claim 7 wherein the first port is integrally formed with the stabilizer member.

9. The cuff of claim 1 wherein the first port is located in close proximity to the first slot.

10. The cuff of claim 9 wherein the first port and first slot are laterally aligned.

11. The cuff of claim 10, further comprising an elongated strip attached at opposing edges thereof across the cuff top surface between the first port and a side edge of the cuff, thereby defining the first slot in lateral alignment with the first port.

12. The cuff of claim 8 wherein the first port is disposed on an attachment region that extends beyond the width of the cuff.

13. A method of constructing an inflatable tourniquet cuff that has a top surface and a width, comprising the steps of:
(a) connecting a port to an elongated inflatable tourniquet cuff;
(b) attaching a fastener to extend from an inflatable first end of the cuff;
providing a slot at a second end of the cuff that is opposite to the first end; and
(d) sizing the slot for permitting the fastener and inflatable first end of the inflatable tourniquet cuff to slide therethrough so that the fastener is located between the first and second ends and is engageable with the top surface of the cuff, resulting in an overlapped surface aligned along long axes of the top surface of the cuff between the first end of the cuff and the second end of the cuff;
(e) connecting together the inflatable cuff with another inflatable cuff that is constructed in accord with steps (a)-(d) above.

14. The method of claim 13 including the step of attaching an elongated strip to the cuff at opposing edges of the strip so that the strip extends across the width of the cuff top surface to provide the slot.

15. The method of claim 13 including the step of sizing the slot to enclose the first end of the cuff that is slid therethrough, thereby to restrict the first end of the cuff from moving sideways relative to the cuff width.

16. The method of claim 13 including the step of shielding part of the cuff top surface to prevent the fastener from engaging the top surface of the cuff when the fastener is slid through the slot.

17. The method of claim 13 including the step of locating the port in close proximity to the slot.

* * * * *